US00PP15777P2

(12) United States Plant Patent
Sakazaki

(10) Patent No.: US PP15,777 P2
(45) Date of Patent: May 31, 2005

(54) ***MECARDONIA* PLANT NAMED 'USMECA67'**

(50) Latin Name: ***Mecardonia caespitosa*×*Mecardonia dianthera***
Varietal Denomination: USMECA67

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 10/839,208

(22) Filed: May 5, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Mecardonia* plant named 'USMECA67', characterized by its vigorous, low-growing, outwardly spreading and trailing plant habit; freely and continuous branching habit; numerous bright yellow-colored flowers; and good garden performance.

1 Drawing Sheet

Botanical classification/cultivar designation: *Mecardonia caespitosa*×*Mecardonia dianthera* cultivar USMECA67.

BACKGROUND OF THE INVENTION

The present Invention relates to a new and distinct cultivar of Sutera plant, botanically known as *Mecardonia caespitosa*×*Mecardonia dianthera,* and hereinafter referred to by the cultivar name 'USMECA67'.

The new Sutera is a product of a planned breeding program conducted by the Inventor in Hikone, Shiga, Japan. The objective of the breeding program is to create new vigorous low-growing *Mecardonias* with freely branching habit and bright yellow-colored flowers.

The new *Mecardonia* originated from a cross-pollination made by the Inventor on May 19, 1999 of an unidentified selection of *Mecardonia caespitosa,* not patented, as the female, or seed, parent with an unidentified selection of *Mecardonia dianthera,* not patented, as the male, or pollen, parent. The new *Mecardonia* was chosen as a single plant from the resulting progeny of the cross-pollination by the Inventor on Jun. 10, 2000, in a controlled environment in Bonsall, Calif.

Asexual reproduction of the new cultivar by terminal cuttings in Bonsall, Calif. since Jul. 1, 2000, has shown that the unique features of this new *Mecardonia* are stable and reproduced true to type in successive generations.

SUMMARY OF THE INVENTION

Plants of the cultivar USMECA67 have not been observed under all possible environmental conditions. The phenotype may vary somewhat with variations in environment such as temperature and light intensity without, however, any variance in genotype.

The following traits have been repeatedly observed and are determined to be the unique characteristics of 'USMECA67'. These characteristics in combination distinguish 'USMECA67' as a new and distinct cultivar of *Mecardonia:*

1. Vigorous, low-growing, outwardly spreading and trailing plant habit.
2. Freely and continuous branching habit.

3. Numerous bright yellow-colored flowers.
4. Good garden performance.

Plants of the new *Mecardonia* are most similar to plants of the parent selections. Compared to plants of the female parent selection, plants of the new *Mecardonia* are more vigorous and flower for a longer period of time. Compared to plants of the male parent selection, plants of the new *Mecardonia* have larger flowers and flower for a longer period of time.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the colors of the new *Mecardonia.*

The photograph at the top of the sheet comprises a side perspective view of three typical flowering plants of 'USMECA67' grown in a container.

The photograph at the bottom of the sheet comprises a close-up view of typical flowers and leaves of 'USMECA67'.

DETAILED BOTANICAL DESCRIPTION

The aforementioned photographs and following observations and measurements describe plants grown in Bonsall, Calif., in an outdoor nursery under full sunlight conditions during the spring and summer with day temperatures ranging from 18 to 35° C. and night temperatures ranging from 7 to 18° C. After planting rooted cuttings, plants were grown for about four weeks in 15-cm containers. Color references are made to The Royal Horticultural Society Colour Chart, 1995 Edition, except where general terms of ordinary dictionary significance are used.

Botanical classification: *Mecardonia caespitosa*× *Mecardonia dianthera* cultivar USMECA67.

Parentage:

*Female parent.*—Unidentified selection of *Mecardonia caespitosa,* not patented.

*Male parent.*—Unidentified selection of *Mecardonia dianthera,* not patented.

Propagation:

*Type cutting.*—Terminal vegetative cuttings.

*Time to initiate roots.*—About two weeks at 22° C.

*Time to produce a rooted cutting.*—About three to four weeks at 22° C.

*Root description.*—Fine; white in color.

*Rooting habit.*—Freely branching.

Plant description:

*Form.*—Low-growing, outwardly spreading and trailing plant habit. Freely and continuously branching with about three to four primary lateral branches each with about two to three secondary lateral branches. Vigorous growth habit.

*Plant height.*—About 10 cm.

*Plant diameter, single plant.*—About 12 cm by 30 cm.

*Lateral branches.*—Length: About 30 cm. Diameter: About 2 mm. Internode length: About 1.5 cm. Texture: Smooth, glabrous. Color: 144A.

*Foliage description.*—Arrangement: Opposite; simple. Length: About 2.1 cm. Width: About 2.2 cm.

*Shape.*—Rounded elliptical.

*Apex.*—Broadly acute.

*Base.*—Attenuate.

*Margin.*—Serrate.

*Texture, upper and lower surfaces.*—Smooth, glabrous.

*Venation pattern.*—Pinnate, arcuate.

*Color.*—Developing and fully expanded foliage, upper surface: 147A. Developing and fully expanded foliage, lower surface: 147B. Venation, upper surface: 145A. Venation, lower surface: 145B.

*Petiole length.*—About 3 mm.

*Petiole diameter.*—About 2 mm.

*Petiole color.*—144A.

Flower description:

*Flower type and habit.*—Solitary axillary flowers on long peduncles; zygomorphic. Flowers persistent. Freely flowering; typically about eight open flowers and about 16 to 20 flower buds per lateral branch. Flowers face mostly outward and upright.

*Natural flowering season.*—Plants typically flower during the spring and summer; flowering continuous during this period.

*Flower longevity on the plant.*—About five days.

*Fragrance.*—None detected.

*Flower size.*—Diameter: About 1.4 cm by 1.6 cm. Length: About 1 cm.

*Flower buds.*—Length: About 1 cm. Diameter: About 6 mm. Shape: Ovoid. Color: 5B.

*Corolla.*—Quantity/arrangement: Four petals fused at the base. Upper and lateral petals, lobe length from throat: About 7 mm. Lower petal, lobe length from throat: About 9 mm. Upper and lateral petals, lobe diameter: About 8 mm. Lower petal, lobe diameter: About 1 cm. Petal lobe shape: Roughly cordate. Petal lobe apex: Slightly emarginate. Petal lobe margin: Entire. Texture, upper and lower surfaces: Smooth, glabrous; satiny. Color: When opening, upper surface: 5A. When opening, lower surface: 5D. Fully opened, upper surface: 7A; lateral and lower petals with hair-like stripes towards the throat, 79B. Fully opened, lower surface: 5D. Flower throat (inside): 7A. Flower tube (outside): 5D.

*Sepals.*—Quantity per flower: Two. Length: About 9 mm. Width: About 1.5 mm. Shape: Linear. Apex: Acute. Margin: Entire. Texture, upper and lower surfaces: Smooth, glabrous. Color, upper and lower surfaces: 144A.

*Flower bracts.*—Quantity per flower: Three. Length: About 8 mm. Width: About 6 mm. Shape: Elliptical. Apex: Acute. Margin: Slightly serrate. Texture, upper and lower surfaces: Smooth, glabrous. Color, upper and lower surfaces: 144A.

*Peduncles.*—Length: About 4.7 cm. Width: About 1 mm. Angle: About 30 to 45° from the stem. Strength: Moderately strong; slender. Texture: Smooth. Color: 144A.

*Reproductive organs.*—Stamens: Quantity per flower: Four to five. Anther shape: Oval. Anther length: Less than 1 mm. Anther color: 155D. Pollen amount: Scarce. Pollen color: 155D. Pistils: Quantity per flower: One. Pistil length: About 5 mm. Style length: About 2 mm. Style color: 145A. Stigma shape: Curved. Stigma color: 145A. Ovary color: 145A.

*Seed/fruit.*—Seed and fruit production has not been observed.

Disease/pest resistance: Plants of the new *Mecardonia* have not been noted to be resistant to pathogens or pests common to *Mecardonia.*

Garden performance: Plants of the new *Mecardonia* have been observed to have good garden performance. Plants of the new *Mecardonia* tolerate temperatures from −4 to 38° C. and have good tolerance to wind and rain.

It is claimed:

1. A new and distinct cultivar of *Mecardonia* plant named 'USMECA67', as illustrated and described.

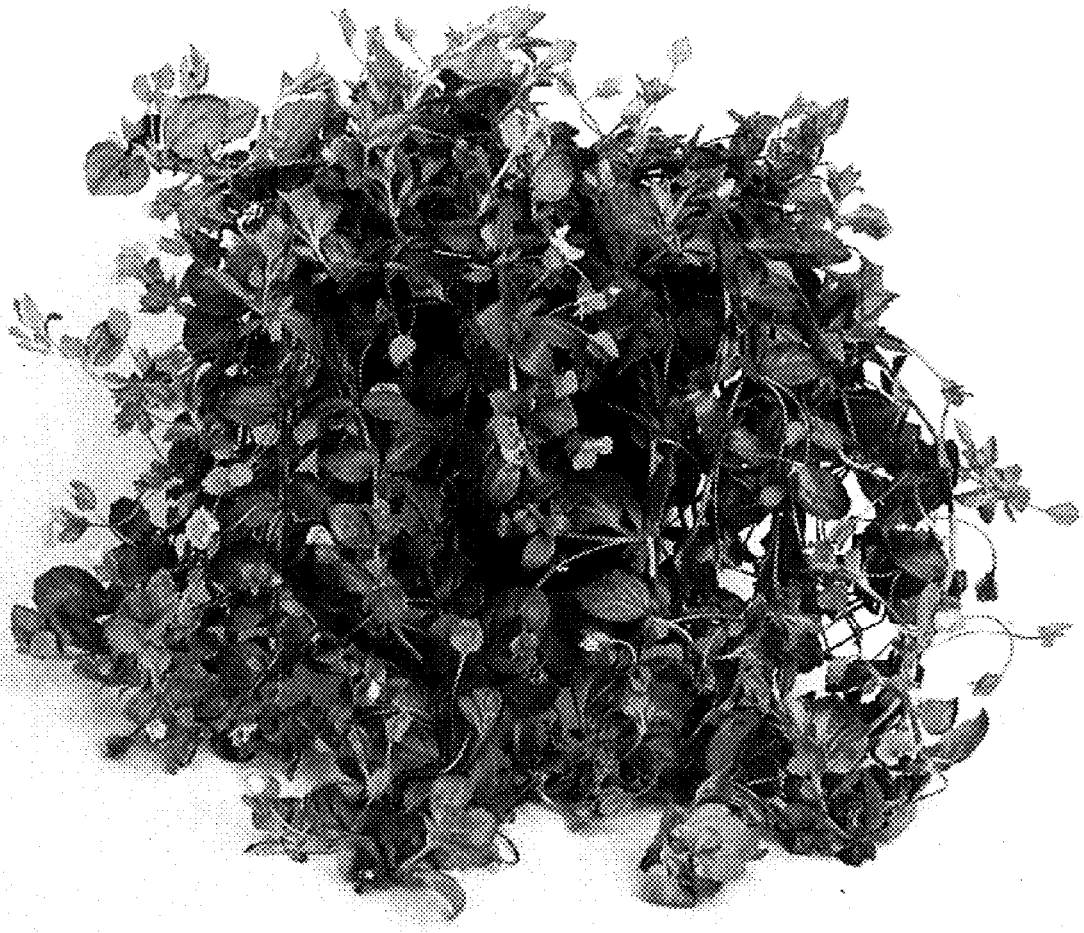
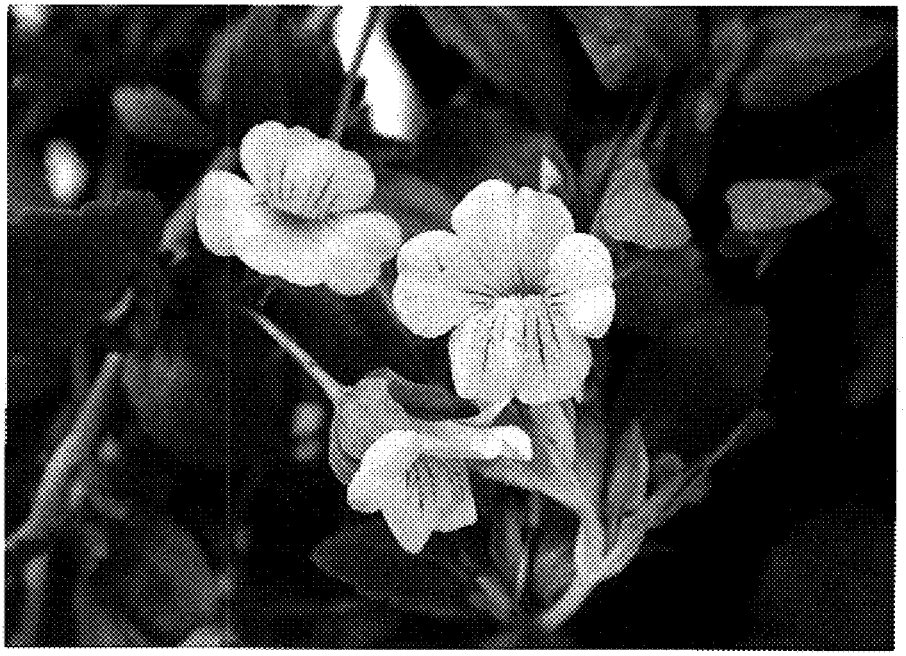

* * * * *